(12) United States Patent
Carmeli et al.

(10) Patent No.: US 6,414,708 B1
(45) Date of Patent: Jul. 2, 2002

(54) VIDEO SYSTEM FOR THREE DIMENSIONAL IMAGING AND PHOTOGRAMMETRY

(75) Inventors: Ran Carmeli, Petach Tikya; Michel Dadi, Herzelia, both of (IL)

(73) Assignee: Dentop Systems, Ltd., Rosh Ha'ayin (IL)

(*) Notice: Subject to any disclaimer, the term of this patent is extended or adjusted under 35 U.S.C. 154(b) by 0 days.

(21) Appl. No.: 09/017,771

(22) Filed: Feb. 3, 1998

(30) Foreign Application Priority Data

Mar. 2, 1997 (IL) .................................... 120135

(51) Int. Cl.[7] .................................. H04N 7/18
(52) U.S. Cl. .................. 348/42; 348/45; 348/49; 348/56; 348/66; 433/31
(58) Field of Search .................. 348/42, 45, 47, 348/49, 66, 56; 433/29, 30, 31

(56) References Cited

U.S. PATENT DOCUMENTS

| | | | |
|---|---|---|---|
| 4,051,534 A | * 9/1977 | Dukich et al. | 348/211 |
| 4,395,731 A | * 7/1983 | Schoolman | 348/53 |
| 4,516,157 A | 5/1985 | Campbell | 348/158 |
| 4,779,965 A | * 10/1988 | Beecher | 359/720 |

* cited by examiner

*Primary Examiner*—Howard Britton
(74) *Attorney, Agent, or Firm*—Needle & Rosenberg, P.C.

(57) ABSTRACT

A video system for providing an operator with a three dimensional stereoscopic image of the oral cavity of a patient is provided. The system includes an imaging unit for providing at least two stereoscopic images of the oral cavity, a pair of switchable shutters for alternatingly blocking the view of the left eye and the right eye of the operator, a synchronizing unit for synchronizing the switching of the pair of switchable shutters with the rate of generation of the two stereoscopic video images by the imaging unit and a video display for displaying the two stereoscopic images.

12 Claims, 15 Drawing Sheets

VIDEO SYSTEM FOR THREE DIMENSIONAL IMAGING AND PHOTOGRAMMETRY

This application claims the benefits of Israel Patent Application No. 120135, filed Mar. 2, 1997.

FIELD OF THE INVENTION

The present invention relates to the field of three dimensional imaging in general, the field of three dimensional (3D) video imaging in particular and specifically to three dimensional imaging systems for dentistry.

BACKGROUND OF THE INVENTION

The use of video cameras in dentistry is a well known in the prior art. Different types of video cameras are used by dentists for viewing the oral cavity, magnifying the view thereof and for recording video images of the oral cavity or selected parts thereof.

Dentists routinely use an inter-oral camera (IOC) inserted into the patients mouth for inter-oral photography. An IOC is usually used in teeth implantation for obtaining exact video photographs used for the precise measurements and three dimensional reconstruction needed for preparing the rehabilitation infrastructure.

Unfortunately, inter-oral cameras need to be sterilized before each use. The camera and the handpiece cannot be sterilized, thus forcing the use of impeding sterilizable plastic enclosures, an expensive and time consuming procedure.

Additionally, inter-oral cameras lack zooming capacity due to the limited possible size of the lens. Some IOC's have a limited capacity for up to three different magnification levels but no continuous zooming capacity. Furthermore, the large size of the handpiece and the power-cord of inter-oral cameras is obstructive to the practitioner performing dental work.

U.S. Pat. No. 4,395,731 to Schoolman discloses the combination of a pair of video cameras and video screens, mounted on a users head to provide a microscope for surgeons. In this arrangement, however, the surgeon does not see the real world, but sees only the image displayed on the video screens directly in front of his eyes.

U.S. Pat. No. 4,516,157 to Campbell discloses a portable electronic camera. This invention teaches an electronic video device including a pair of spectacles adapted to be worn on a user's head and having the object of providing a readily portable electronic video means for recording video images in which the video image substantially corresponds to the view directly seen by the operator wearing the device.

Dentists practicing the fitting of fixed prostheses supported by osseo-integrated implants routinely perform photogrammetric measurements of implant positions. Such measurements require the use of specially adapted cameras for taking still photographs of the implants followed by photogrammetric measurements of the developed film. This method requires precision manual photogrammetric measurement and calibration techniques which are time consuming, expensive and which requires considerable expertise. Additionally, prior art of photogrammetric measurement of implant positions requires developing the film before measurements can be performed, adding to the cost and duration of the procedure.

SUMMARY OF THE PRESENT INVENTION

It will be appreciated by those skilled in the art that although the 3D video viewing system disclosed hereinbelow in accordance with the preferred embodiments of the present invention is adapted for use by dentists, certain aspects of the invention are equally applicable to other types of use. The system can also be generally adapted for use in any application where a system is needed to enable a person to view objects two-dimensionally or three-dimensionally on a video display, with or without zooming capability, while having both hands free to manipulate the objects and while retaining the possibility of direct visual control of the objects. For example the system can be used for inspection and repair of electronic circuit boards, for assembling or taking apart of multi-component mechanical devices such as watches or any other mechanical devices or for surgery.

One object of the present invention is to provide a video system for providing a dentist with a three-dimensional or two-dimensional video image of the oral cavity of a patient.

A feature of a preferred embodiment of the present invention is the use of a video system placed outside of the oral cavity of the patient, thus allowing the dentist unobstructed access to the oral cavity.

A feature of another preferred embodiment of the present invention is the use of a zooming video system for providing a user controlled, variable magnification of the image of the oral cavity.

Another object of the present invention is to provide a video system for producing a composite video image composed of three different superimposed video images, each of the three video images taken from a different angle of view. The composite video image can be fed to a host computer for performing various photogrammetric measurements thereon, thus obviating the use of a photogrammetric still camera and the processing of the film.

A feature of a preferred embodiment of the present invention is that the video system which is used for providing a three dimensional video image of the oral cavity, can also be used for providing a composite video image for photogrammetric measurements, thus obviating the need for a separate photogrammetric camera.

There is therefore provided, in accordance with a preferred embodiment of the present invention, a video system for providing an operator with a three dimensional stereoscopic image of the oral cavity of a patient. The system includes an imaging unit for providing at least two stereoscopic images of the oral cavity, a pair of switchable shutters for alternatingly blocking the view of the left eye and the right eye of the operator, a synchronizing unit for synchronizing the switching of the pair of switchable shutters with the rate of generation of the two stereoscopic video images by the imaging unit and a video display for displaying the two stereoscopic images.

Further, in accordance with another preferred embodiment of the present invention, the imaging unit of the video system includes a video camera and an optical assembly disposed between the video camera and the oral cavity for alternatingly providing the video camera with at least two different stereoscopic images of the oral cavity in synchrony with the field rate of the video camera.

Further, in accordance with yet another preferred embodiment of the present invention, the optical assembly is also operative to simultaneously provide a first image of the oral cavity along a first optical axis of the optical assembly, and a pair of second and third stereoscopic images of the oral cavity along a second and third optical axes of the optical assembly, respectively. The second and third optical axes are inclined at an angle to the first optical axis, and the three different images are superimposed upon the imager of the video camera to provide a composite video image.

Additionally, in accordance with yet another preferred embodiment of the present invention, the synchronizing unit also digitizes the composite video image and provides a host computer with a digitized composite video image for performing photogrammetric measurements thereon.

Furthermore, in accordance with still another preferred embodiment of the present invention, the imaging unit comprises two video cameras providing a pair of stereoscopic images of the oral cavity and the synchronizing unit synchronizes the two video cameras with the switching rate of the switchable shutters.

Furthermore, in accordance with another preferred embodiment of the present invention, the imaging unit also includes two folding mirrors for folding the light reflected from the oral cavity towards the two video cameras.

Furthermore, in accordance with yet another preferred embodiment of the present invention, the imaging unit is attached to a harness worn on the head of the operator.

Furthermore, in accordance with still another preferred embodiment of the present invention, the video system also includes a folding mirror for folding the light reflected from the oral cavity towards the imaging unit.

Further yet, in accordance with another preferred embodiment of the present invention, the synchronizing unit provides multiplexed left and right video image signals to the video display at a rate which is double the field rate of the video camera for providing the operator with a flicker-free image of the oral cavity on the video display.

Furthermore, in accordance with yet another preferred embodiment of the present invention, the switchable shutters are liquid-crystal shutters.

Further yet, in accordance with still another preferred embodiment of the present invention, the video camera further comprises a zoom lens controllable by the operator for providing the three dimensional stereoscopic images and the composite video image at a selectable magnification.

There is also provided, in accordance with still another preferred embodiment of the present invention, a video system for providing an operator with a two-dimensional video image of the oral cavity of a patient. The video system includes a harness wearable on the head of the operator, a video camera attached to the harness for imaging the oral cavity and a video display connected to the video camera for displaying the video image.

Further yet, in accordance with still another preferred embodiment of the present invention, the video camera further comprises a zoom lens controllable by the operator for providing the two-dimensional stereoscopic images at a selectable magnification.

Finally, in accordance with still another preferred embodiment of the present invention, the two-dimensional video system further includes a folding mirror for directing the light from the oral cavity to the video camera.

BRIEF DESCRIPTION OF THE DRAWINGS

The present invention will be understood and appreciated more fully from the following detailed description taken in conjunction with the drawings in which.

DETAILED DESCRIPTION OF A PREFERRED EMBODIMENT

Figure 1:
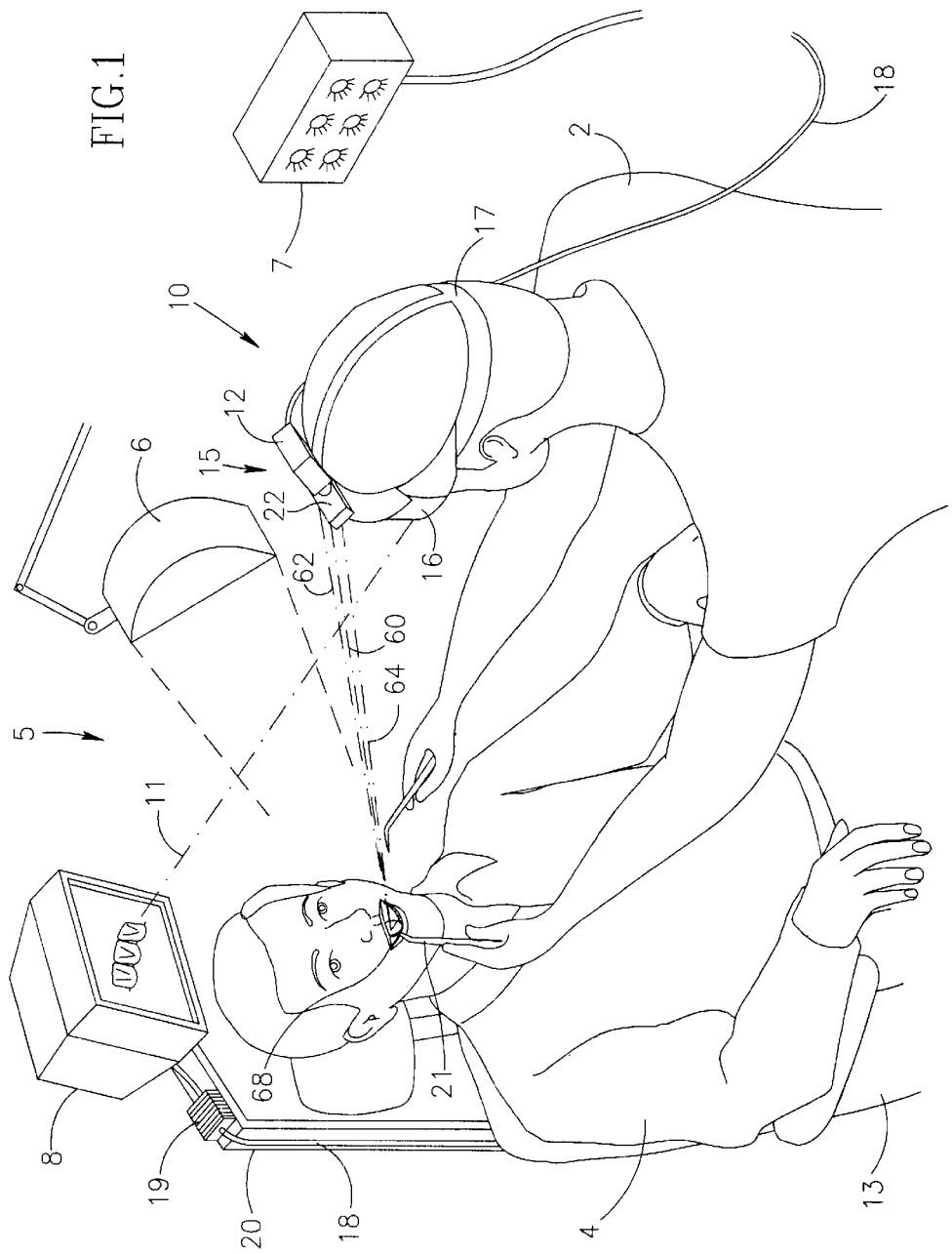
FIG. 1 is an isometric view of a three dimensional (3D) stereoscopic video system for 3D viewing and for photogrammetric video photography in accordance with a preferred embodiment of the present invention.

Reference is now made to FIG. 1 which is an isometric view of a three dimensional (3D) stereoscopic video system, generally referred to as video system 5 hereinafter, for 3D viewing and for photogrammetric video photography. The system 5 is capable of providing 3 different angular views of a viewed object in accordance with a preferred embodiment of the present invention. The video system 5 is shown as used by a dentist 2 while working on a patient 4. The video system 5 includes a headset 10 worn on the head of the dentist 2 for providing three dimensional imaging capability. The video system 5 also includes a video display 8 supported by display stand 20 for displaying a video image of the oral cavity 68. The display stand 20 is attached to a chair 13. Patient 4 sits on the chair 13 while being treated by the dentist 2. It is noted that the video display 8 can also be positioned at any suitable position such as above the head of the patient 4 or at the side of the patient 4.

The headset 10 includes an imaging unit 15 and a pair of liquid crystal shutters (LCS) spectacles 16 operative to enable 3D visualization of the images presented on the video display 8 as described in detail hereinafter. The imaging unit 15 includes a video camera 12 suitably attached to an optical assembly 22 for obtaining a video image of the oral cavity 68 of patient 4 which is presented on the video display 8. The head set 10 further includes a head mountable harness 17. The imaging unit 15 is adjustably attached to the harness 17. The LCS spectacles 16 are separate from the harness 17 of the headset 10 as shown in FIG. 1. It is noted that the LCS spectacles can also be attachable to the harness 17 of the head set 10 or can be an integral part of the harness 17 of headset 10.

Figure 2:
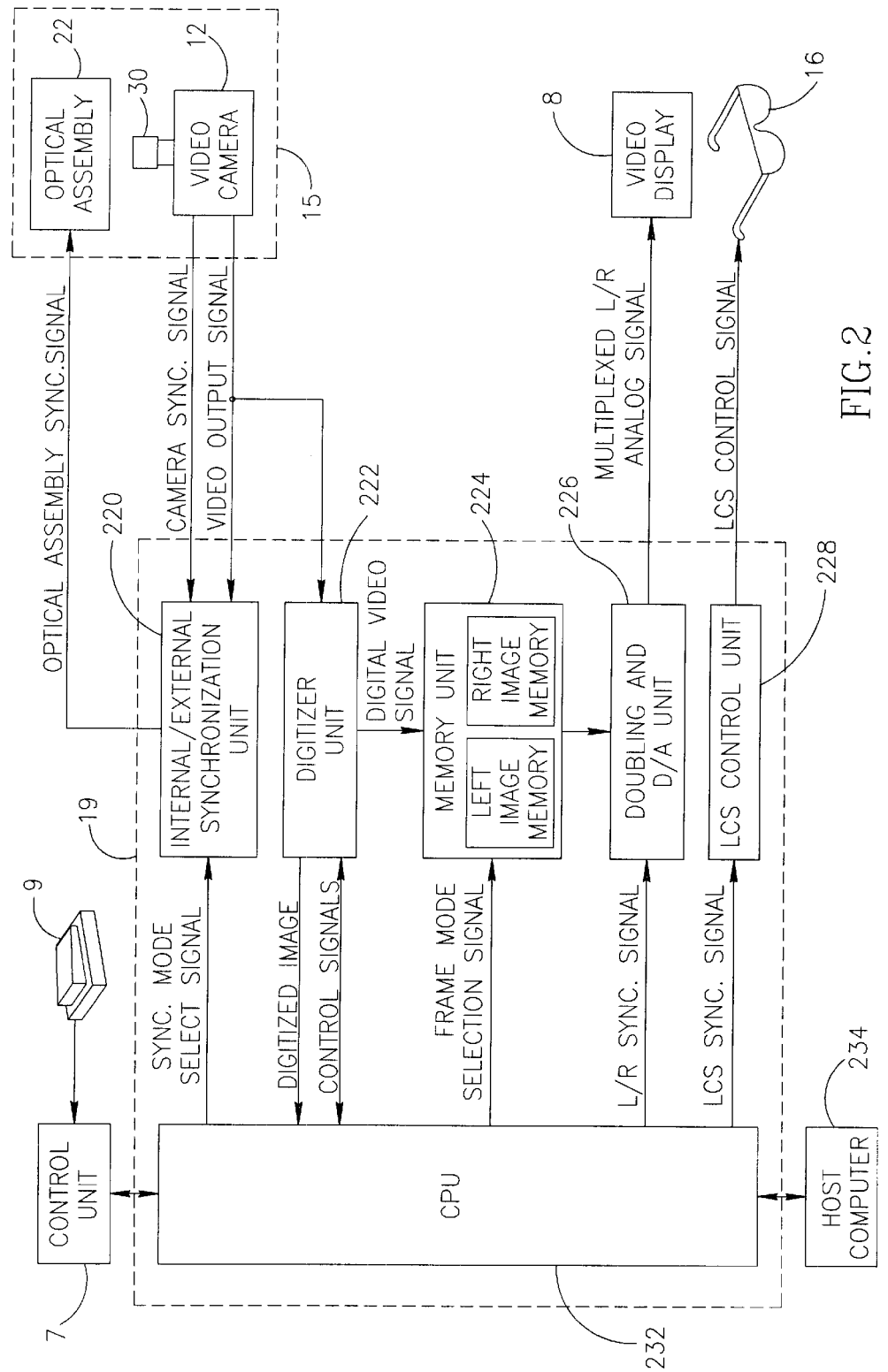
FIG. 2 is a schematic block diagram illustrating the details of the synchronizing unit the of the 3D stereoscopic video system of FIG. 1 in accordance with a preferred embodiment of the present invention.

Reference is now made to FIG. 2 which is a schematic block diagram illustrating the connections between the various components of the video system 5 of FIG. 1. The synchronizing unit 19 is connected to the LCS spectacles 16 and to the optical assembly 22 for synchronizing the switching of the various LCS shutters included in the LCS spectacles 16 and the optical assembly 22 as disclosed in detail hereinbelow. The video camera 12 is connected to the video display 8 by a cable 18 and the synchronizing unit 19 for communicating the video signals from the video camera 12 to the video display 8. The video system 5 also includes a system control unit 7 for controlling the operation of the various components of the video system 5. The control unit 7 is connected to the video camera 12 for controlling the image magnification. The control unit 7 is also connected to the synchronizing unit 19 for controlling the switching rate of the LCS elements 26, 28, 38, 40, and 50. Additionally the control unit 7 is connected to a foot pedal 9 for controlling the operation of the video system 5.

It is noted that for the sake of clarity of illustration the foot pedal 9 and some of the different cables connecting the components of the video system 5 are not shown in FIG. 1.

The synchronizing unit 19 includes a CPU 232 suitably connected to the control unit 7 and to an internal/external synchronization unit 220 for synchronizing the operation of the video camera 12 with the operation of the LCS spectacles 16 and the elements of the optical assembly 22 as is disclosed in detail hereinafter. The CPU 232 is also connected to a digitizer unit 222 for digitizing output of the video camera 12. The digitizer unit 222 is connected to a memory unit 224 for storing the digitized images. The memory unit 224 is connected to CPU 232 for receiving suitable mode selection signals therefrom. The memory unit 224 is also connected to a doubling and D/A unit 226 which is connected to CPU 232 for receiving synchronization signals therefrom and to video display 8 for sending the analog multiplexed left/right video signals thereto. The CPU 232 is also connected to an LCS control unit 228 which is also connected to LCS spectacles 16. Additionally, CPU 232 can be connected to a host computer 234 for storing and retrieving data. The synchronizing unit 19 can be used for providing 3D video images by being connected to a single camera and an optical assembly (FIG. 1) or by being connected to two video cameras as disclosed in detail hereinafter.

Returning to FIG. 1, the video system 5 also includes a light source 6 suitably arranged to illuminate the oral cavity 68 of the patient 4. The light source can be any suitable light source that can be positioned at any suitable position for illuminating the oral cavity 68 of the patient 4.

When the dentist 2 is using the headset 10 he can adjust the position of the imaging unit 15 so that it is properly oriented to pick up the image of the oral cavity 68 of the patient 4 while the dentist is looking at the video display 8 along a line of sight 11. An advantage of this preferred embodiment is that the dentist can freely shift his line of sight at any time so as to view the three dimensional image of the oral cavity presented on the video display 8 or any other part of the "real world" such as the real oral cavity. Thus the LCS spectacles 16 enable the dentist to see any desired object in the real world as well as to see a three dimensional and selectably magnified image of the oral cavity by looking at the video display 8.

It is noted that, for a better understanding, like components are designated by like reference numerals throughout the various figures.

Figure 3:
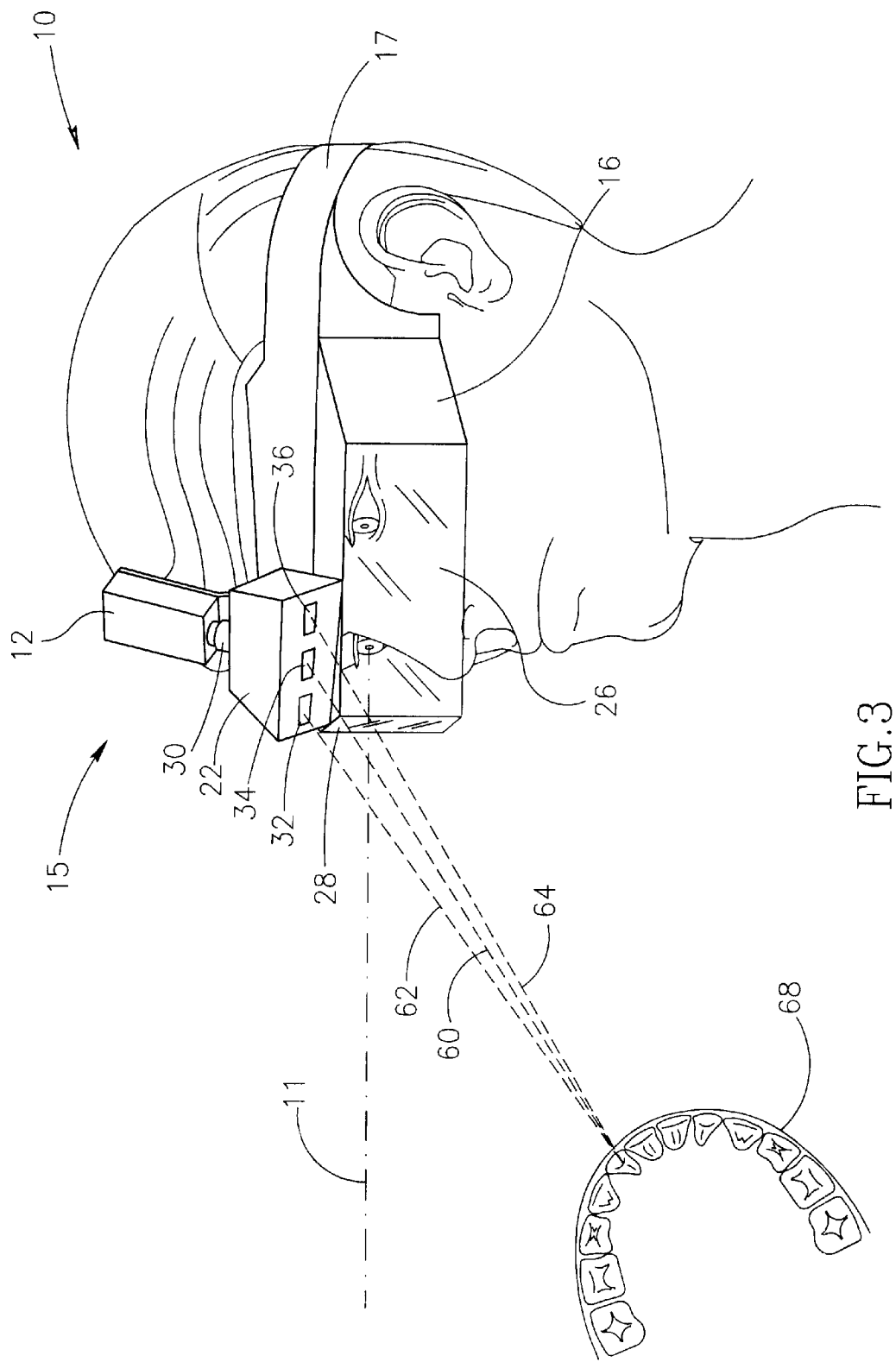
FIG. 3 is a schematic isometric view illustrating in detail the head set of the 3D stereoscopic video system of FIG. 1 in accordance with a preferred embodiment of the present invention.

Reference is now made to FIG. 3 illustrating the head set 10 of FIG. 1 in detail. Video camera 12 includes a lens assembly 30 which is suitably attached to the optical assembly 22. The optical assembly 22 includes three optical windows 32, 34 and 36 through which video images of the oral cavity 68 can be obtained. The LCS spectacles 16 include a left LCS 26 and a right LCS 28 which are positioned in front of the dentist's left and right eyes, respectively.

Figure 4:
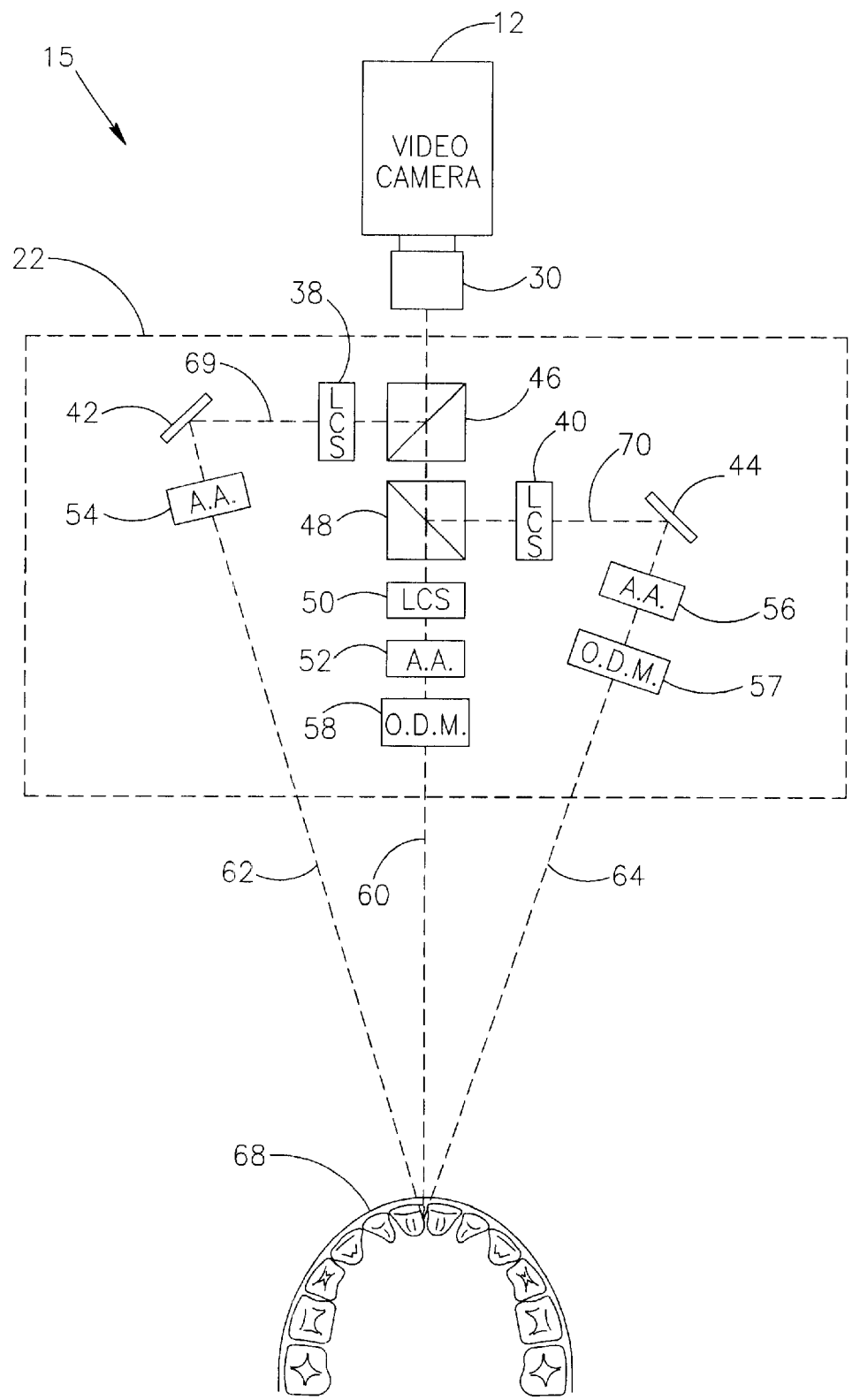
FIG. 4 is a schematic diagram illustrating the optical layout of the imaging unit of the head set of FIG. 3 in accordance with a preferred embodiment of the present invention.

Reference is now made to FIG. 4 which is a schematic diagram of a top view of the imaging unit 15 of head set 10 illustrating the optical layout of the video camera 12, the lens assembly 30 and the optical and electro-optical components of the optical assembly 22.

The optical assembly 22 includes two beam splitters (BS) 46 and 48, an LCS 50, an adjustable attenuator (AA) 52 and an optical distance matcher (ODM) 58, all aligned in that order in front of the lens assembly 30 of video camera 12, along an optical axis 60 which is the optical axis of the lens assembly 30. The optical assembly 22 further includes two folding mirrors 42 and 44 and two adjustable attenuators 54 and 56. AA 54 is aligned in front of the folding mirror 42 along an optical axis 62, and AA 56 is aligned in front of the folding mirror 44 along an optical axis 64. The optical assembly 22 additionally includes an ODM 57 aligned in front of AA 56 along the optical axis 64. The optical assembly 22 further includes an LCS 36 aligned between the folding mirror 42 and the BS 46 along an optical axis 69. The optical assembly 22 also includes an LCS 40 aligned between the folding mirror 44 and the BS 48 along an optical axis 70.

The video camera 12 can acquire a video image of an object such as the oral cavity 68 from three different angles of view represented herein by the optical axes 60, 62 and 64. Thus, light reflected from parts within the oral cavity 68 travels along the optical axis 62, passes through AA 54, is reflected by the folding mirror 42 along optical axis 69, passes through LCS 38 and is reflected by BS 46 along optical axis 60 to reach lens assembly 30 of the video camera 12. Similarly, light reflected from parts within the oral cavity 68 along optical axis 64 passes AA 56, is reflected by the folding mirror 44 along the optical axis 70, passes through LCS 40 and is reflected by BS 48 along optical axis 60 and through BS 46 to reach lens assembly 30. Additionally, light reflected from the parts within the oral cavity 68 along optical axis 60 passes through the ODM 58, the AA 52, the LCS 50 and the BS 48 and 46 to reach lens assembly 30.

Each of the LCS elements 38, 40 and 50 can be suitably switched between two states by the internal/external synchronization unit 220 of FIG. 2. In the first state the light can pass through the LCS and in the second state the light is blocked from passing through the LCS. For example, when the LCS elements 38 and 40 are in the second state and the LCS element 50 is in the first state, the image acquired by the video camera 12 has the angle of view corresponding with the optical axis 60. When the LCS elements 40 and 50 are in the second state and the LCS element 38 is in the first state the image acquired by the video camera 12 has the angle of view corresponding with the optical axis 62. When the LCS elements 38 and 50 are in the second state and the LCS element 40 is in the first state the image acquired by the video camera 12 has the angle of view corresponding with the optical axis 64.

Thus, by suitably switching the LCS elements 38, 40 and 50, the camera 12 can acquire an image of an object such as the oral cavity 68 from any angle of view selected out of the three angles of view corresponding with the three optical axes 60, 62 and 64.

The imaging unit 15 uses the adjustable attenuators 52, 54 and 56 to control the attenuation of light passing along the optical axes 60, 62 and 64, respectively. This is performed in order to equalize the light intensities reaching the lens assembly 30 from each the three different selectable angles of view. This attenuation is necessary since light is differently attenuated along each of the different paths starting at the oral cavity 68 and continuing along the different optical axes 60, 62 and 64. Thus, the system can compensate for the different light intensities of the different light paths by suitably adjusting the attenuation of the light of the different AAs with the result that the intensity of light reaching the lens assembly 30 through each of the three different paths is equal.

ODM 57 and ODM 58 are aligned along optical axes 64 and 60, respectively, and are operative to equalize the path length which is traversed by light traveling along the three different paths.

Going back to FIG. 4, it is noted that the optical assembly 22 includes three optical windows 32, 34 and 36 through which pass the three optical axes 62, 60 and 64, respectively. It is further noted that the distance between the optical windows 32 and 36 is roughly similar to the average human inter-ocular distance.

Returning to FIG. 1, the video system 5 can be operated in two different operating modes. The first mode is a stereoscopic viewing mode which provides the dentist 2 with a three dimensional stereoscopic view of the oral cavity 68 while leaving both of his hands free to use and manipulate various instruments within the oral cavity 68. The second mode is a photogrammetric mode intended for acquiring of the necessary video images required for photogrammetric measurements of implant positions.

In the stereoscopic mode, the dentist 2 wearing the head set 10 adjusts his head position so that the optical axes 60, 62 and 64 of the imaging unit 15 are generally oriented in the direction of the oral cavity 68 of the patient 4. In the stereoscopic mode the synchronizing unit 19 constantly keeps the LCS 50 in the second state, thus, constantly blocking light traveling along optical axis 60 from reaching the lens assembly 30. The synchronizing unit 19 also alternately switches the LCS elements 38 and 40 in such a way that at any point in time only one of the LCS elements 38 or 40 is in the first state while the other LCS element is in the second state. The result of this alternating switching is that the video camera 12 alternately images the oral cavity 68 from one of the two different angles of view, corresponding with the optical axes 62 or 64. The video camera 12, thus alternately sends these different images to be displayed on the video display 8. The synchronizing unit 19 also alternately switches the LCS elements 26 and 28 of the LCS spectacles 16 in such a way that whenever the video display 8 displays the image obtained along the optical axis 64, the synchronizing unit 19 also switches the LCS element 26 to the first state and the LCS element 24 to the second state, thus blocking the view of the right eye of the dentist 2 while permitting the left eye to view the image displayed on the video display 8.

Alternatively, whenever the video display 8 displays the image obtained along the optical axis 62, the synchronizing unit 19 also switches the LCS element 24 to the first state and the LCS element 26 to the second state, thus blocking the view of the left eye of the dentist 2 while permitting the right eye to view the image displayed on the video display 8.

When this alternating switching is performed at an approximate rate of 50 cycles per second per LCS the dentist 2 sees a relatively flicker-free stereoscopic 3D image of the oral cavity 68 or a part thereof, depending on the specific magnification factor of the system. The magnification factor of the system is determined by the focal length of the lens assembly 30, the working distance between the imaging unit and the viewed object and the size of the video camera imager.

It is noted that the lens assembly 30 of the video camera 12 can be any suitable lens such as a lens with a fixed focal length, a lens with multiple focal length settings or a continuously variable zoom lens.

It is further noted that the frequency of alternate switching of the LCS elements can be controlled by the dentist through the control unit 7 or the foot pedal 9 to achieve a flicker-free 3D image of the oral cavity 68.

When the photogrammetric mode is selected by the dentist using the control unit 7, CPU 232 sends an appropriate control signal to the internal/external synchronization unit 220 which suitably switches the three LCS elements 38, 40 and 50 of the optical assembly 22 to the first state so that all the three different images of the oral cavity 68 which are viewed from all three possible angles of view corresponding with the three optical axes 60, 62 and 64, are simultaneously projected on the imager of the video camera 12. Thus, in the photogrammetric mode, a composite image of the oral cavity taken from the three different angles of view is projected upon the imager of the video camera 12. It is noted that the imager (not shown) can be any suitable imager such as a charge coupled device (CCD).

Going back to FIG. 2, the composite image from video camera 12 is digitized by the digitizer unit 222 and can be sent as output to the host computer 234. The composite image can be stored in the host computer 234 for later use in the performing of photogrammetric measurements.

It is noted that when the systems are used in the photogrammetric mode, the acquired images needed for the photogrammetric measurements are preferably obtained by video photography of the upper and lower dental sets in the oral cavity 68 from a viewing point orthogonal to the plane of arrangement of the dental set. This can be performed by the dentist by placing a hand held mirror 21 (FIG. 1) in the oral cavity 68 and suitably orienting the mirror 21 until the required image is viewed on the video display 8 and then initiating the acquisition of the images as described hereinabove. It is noted that composite photogrammetric images can also be obtained by using a properly aligned mirror supported inside the oral cavity by an adjustable mechanical mirror arm (not shown). For example the mirror arm can be attached to the display stand 20 (not shown).

For 3D stereoscopic viewing with a single camera, the synchronizing unit 19 of FIG. 2 synchronizes the operation of the video camera 12, optical assembly 22 video display 8 and LCS spectacles 16. When the dentist selects 3D stereoscopic viewing using the control unit 7, the CPU 232 sends an appropriate control signal to the internal/external synchronization unit 220. The internal/external synchronization unit 220 senses the field rate of the interlaced video output of the video camera 12, synchronizes itself to the sensed field rate and sends appropriate synchronization signals to the optical assembly 22. For example, the synchronization can switch the LCS elements 38 and 40 of optical assembly 22 such that the odd fields are grabbed only for the left optical path (along optical axis 64 of FIG. 1) and the even fields are grabbed only for the right optical path (along the optical axis 62 of FIG. 1), mutatis mutandis. The grabbing is performed by the digitizer unit 222 and the memory unit 224, under the control of the CPU 232. The grabbed image fields from the left and the right optical paths are written into the left image memory and the right image memory of the memory unit 224, respectively.

The doubling and D/A unit 226 reads the digitized video images in the left and right image memories of the memory unit 224 at a rate which is double the rate of the grabbing/writing used by the digitizer unit 222 and the memory unit 224, respectively, and converts the digitized images to analog video signals.

The left and right analog video signals are fed to the video display 8 at the doubled field rate of 100–120 Hz. This doubled rate ensures that a flicker-free image will be viewed on the video display 8 by the user wearing the LCS spectacles 16. Both the doubling and D/A unit 226 and the LCS control unit 228 are controlled by CPU 232 to ensure synchronization of the LCS spectacles 16 at the appropriate doubled rate to match the field rate displayed on the video display 8.

Figure 5:
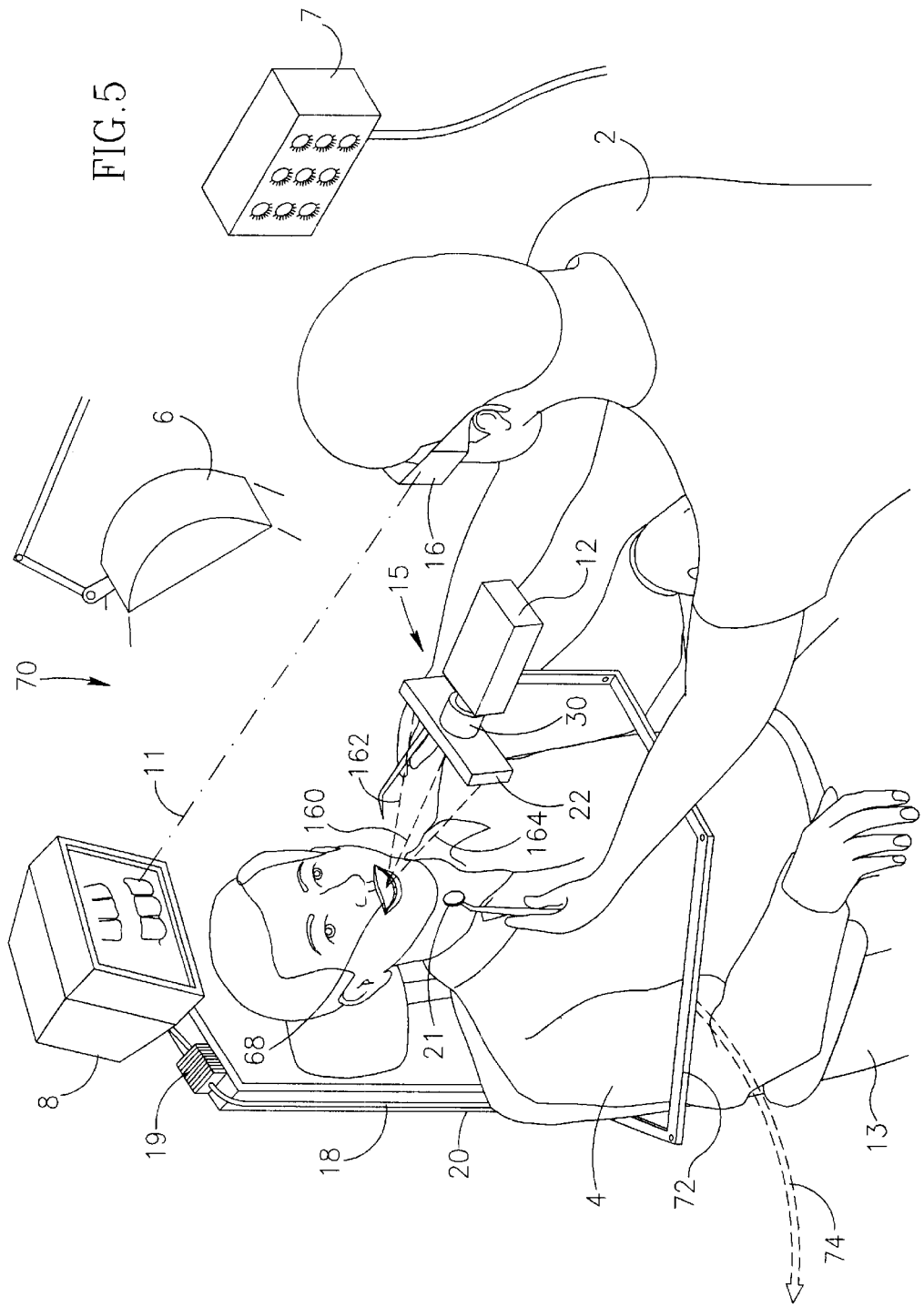
FIG. 5 is an isometric view illustrating a 3D stereoscopic video system in accordance with another preferred embodiment of the present invention.

Reference is now made to FIG. 5 which illustrates a 3D stereoscopic video system in accordance with another preferred embodiment of the present invention. The video system 70 is similar to the video system 5 of FIG. 1 except that the imaging unit 15 is not attached to the harness 17 worn on the head of the dentist 2 but is attached to a supporting arm 72. The supporting arm 72 is attached to the display stand 20 by a hinge (not shown) in such a way that the supporting arm 72 and the imaging unit 15 attached thereto can be rotated along the arrow labeled 74 so that they can be placed in front of the patient 4 or moved to the side of the patient to enable the patient to sit in the chair 13. It is noted that the imaging unit 15 is attached to the supporting arm 72 in such a way that the position of the imaging unit 15 can be adjusted relative to the oral cavity 68 of the patient 4. The imaging unit 15 images the oral cavity 68 along the optical axes 160, 162 and 164. The LCS spectacles 16 are worn by the dentist 2 and operate as disclosed hereinabove.

It is further noted that for the sake of clarity of illustration the various cables connecting the various components of the video system 70 are not shown in FIG. 5.

The video system 70 can operate in the stereoscopic viewing mode and in the photogrammetric mode, as disclosed in detail for the video system 5 hereinabove.

Figure 6:
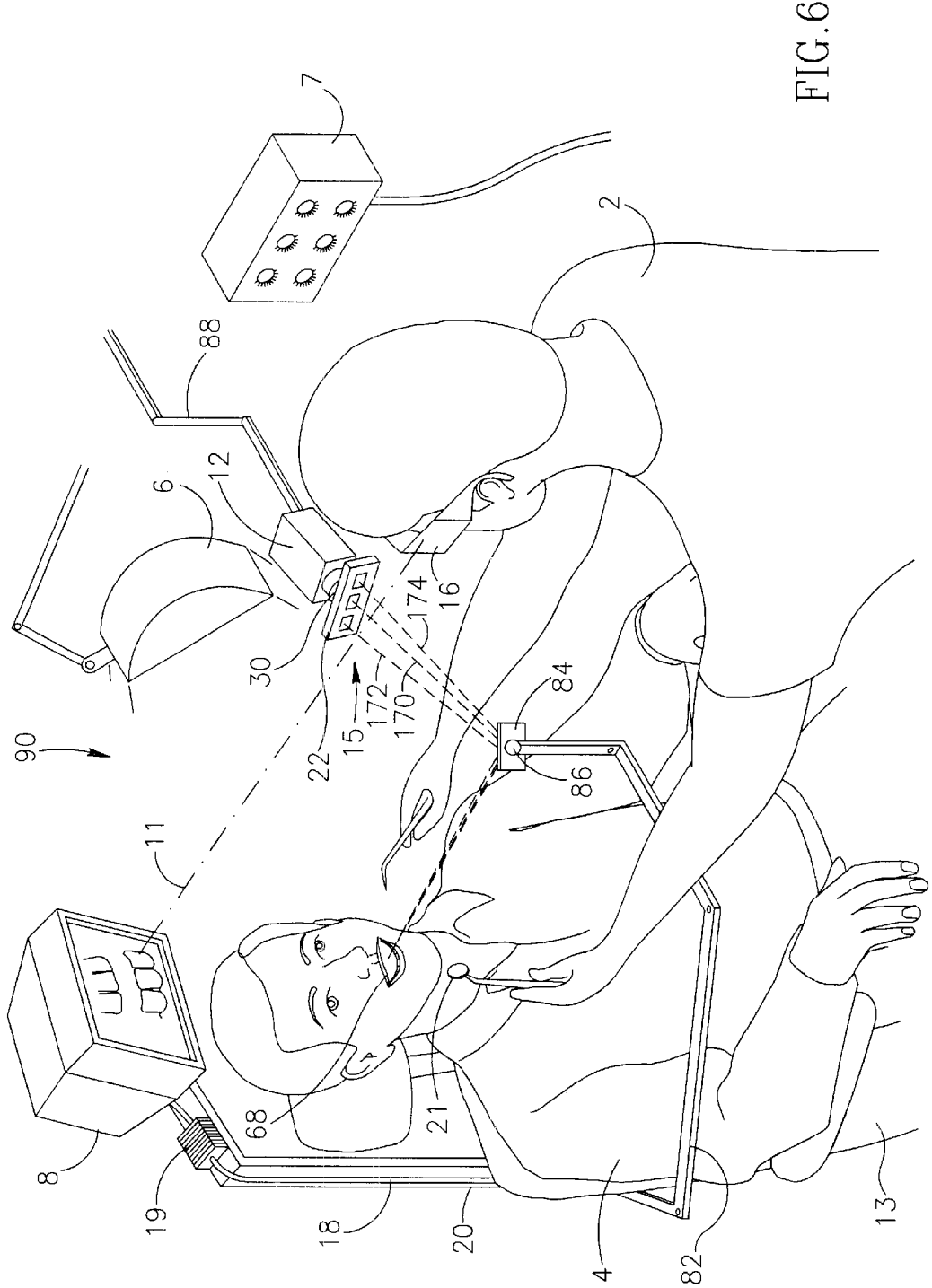
FIG. 6 is an isometric view illustrating an additional 3D stereoscopic video system, in accordance with yet another preferred embodiment of the present invention.

Reference is now made to FIG. 6 which illustrates a 3D stereoscopic video system 90 in accordance with another preferred embodiment of the present invention. The video system 90 is similar to the video system 70 of FIG. 5 except that the imaging unit 15 is not attached to the supporting arm 72 of FIG. 5 but is attached to a supporting arm 88. The supporting arm 88 enables the dentist 2 to position the imaging unit 15 at the side of the patient 4. The video system 90 additionally includes a folding mirror 84 which is connected by a ball joint 86 to a mirror supporting arm 82. The dentist 2 can adjust the position of the folding mirror 84 relative to the imaging unit 15 and the oral cavity 68 to achieve a proper stereoscopic view of the oral cavity while looking at the video display 8 along the line of sight 11 through the LCS spectacles 16. The imaging unit 15 images the oral cavity 68, reflected in the folding mirror 84, along the optical axes 170, 172 and 174. The video system 90 is operative in the stereoscopic viewing mode and in the photogrammetric mode as described in detail for the video system 5 of FIG. 1 hereinabove.

It is noted that the mirror supporting arm 82 is constructed and operative to enable suitable adjustment of the position of the folding mirror 84 at a desired position relative to the oral cavity 68.

Figure 7:
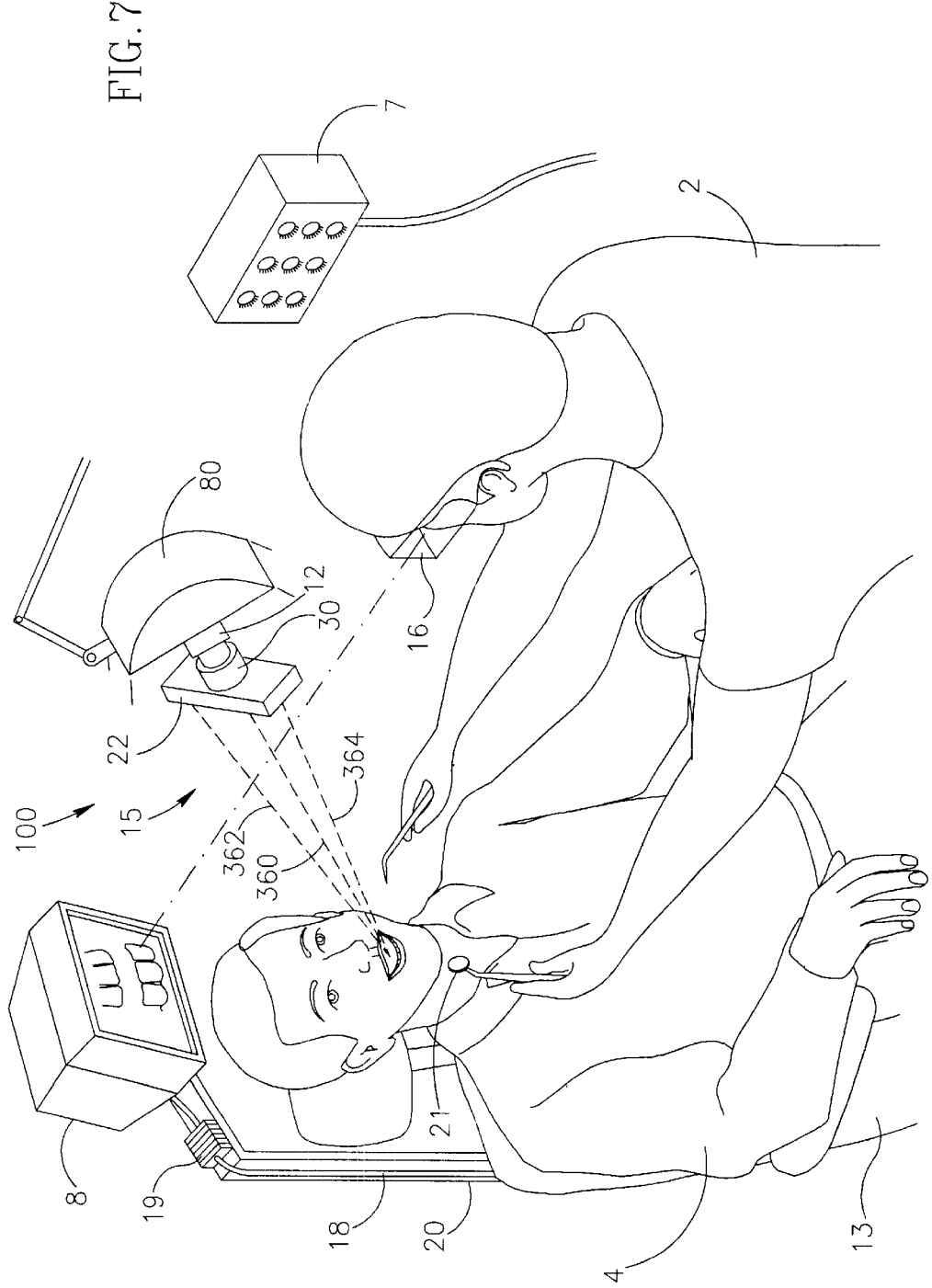
FIG. 7 is an isometric view illustrating another 3D stereoscopic video system, referred to as video system 100 hereinafter, in accordance with another preferred embodiment of the present invention.

Reference is now made to FIG. 7 which illustrates a 3D stereoscopic video system, referred to as video system 100 hereinafter, in accordance with a preferred embodiment of the present invention. The video system 100 is similar to the video system 90 of FIG. 6 except that the imaging unit 15 is attached to a light source 80. The light source 80 enables the dentist 2 to position the imaging unit 15 at a suitable position for imaging of the oral cavity 68 of the patient 4, thus obviating the need for the folding mirror 84, the mirror supporting arm 82 and the supporting arm 88 of FIG. 6. The imaging unit 15 images the oral cavity 68 along the optical axes 360, 362 and 364.

The video system 100 is operative in the stereoscopic viewing mode and in the photogrammetric mode as described in detail for the video system 5 of FIG. 1 hereinabove.

Figure 8:
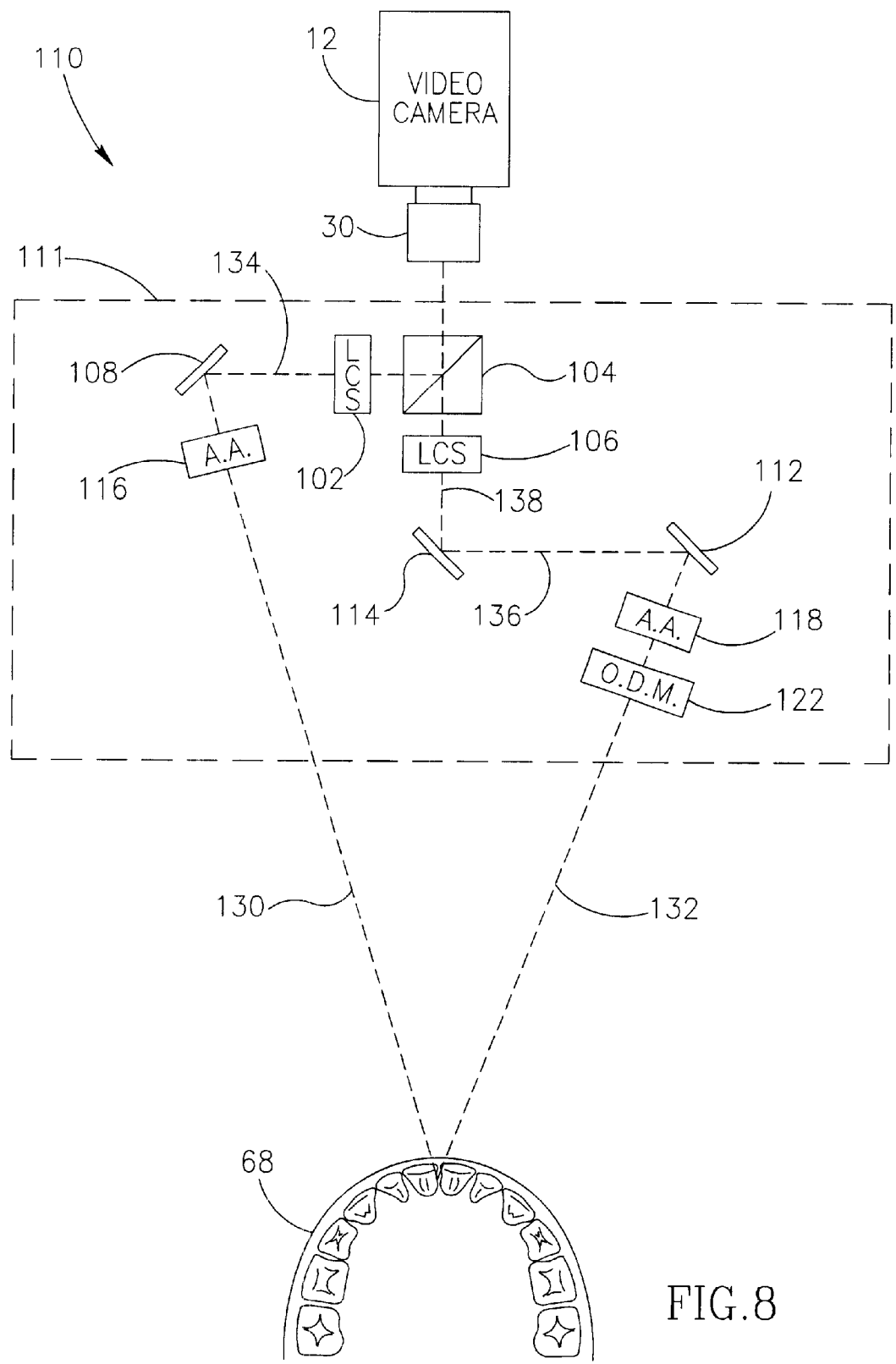
FIGS. 8–10 are schematic diagrams illustrating three additional optical layouts of the imaging unit of the head set of FIG. 3 in accordance with additional preferred embodiments of the present invention.
Figure 9:
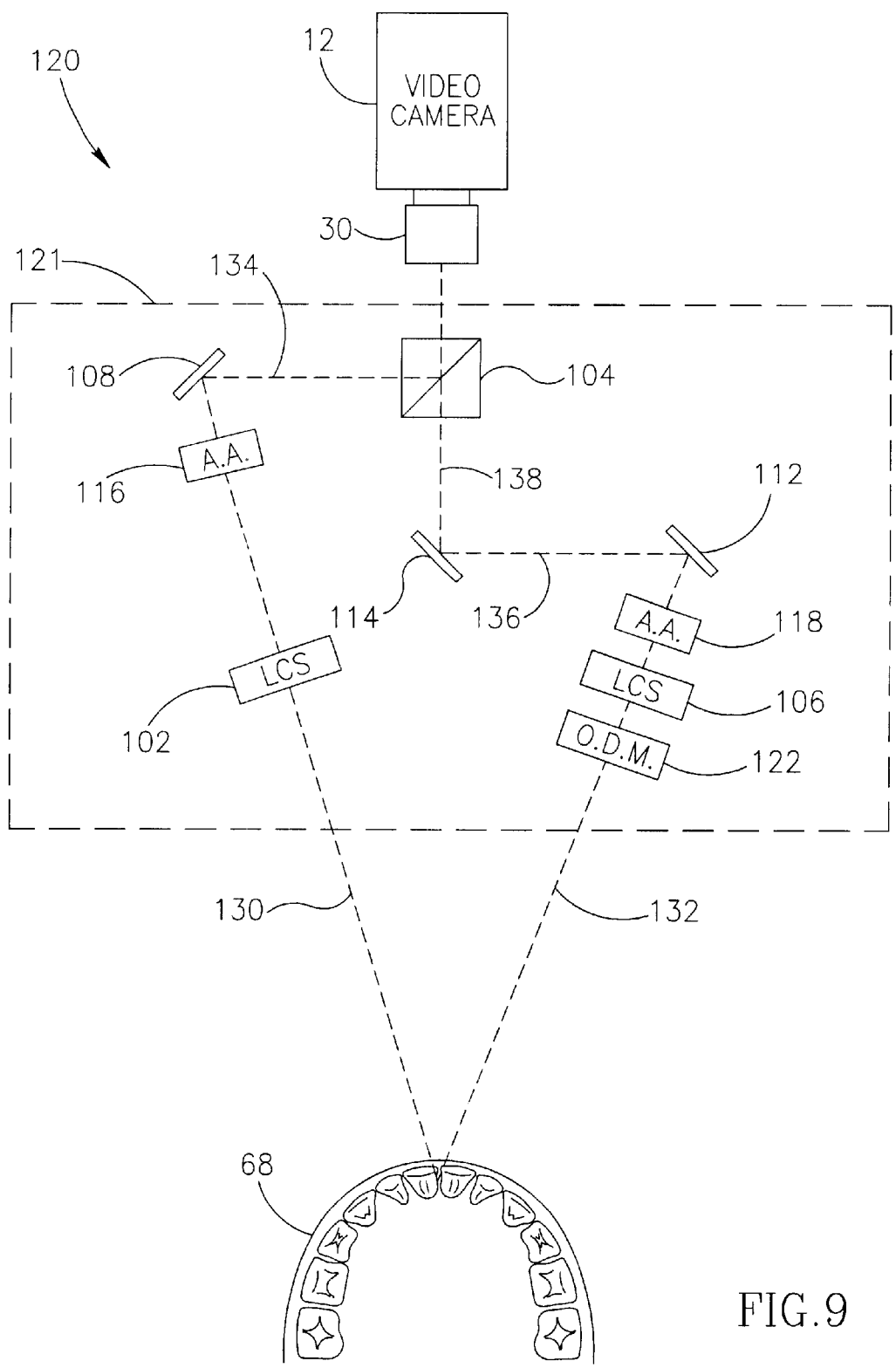
Figure 10:
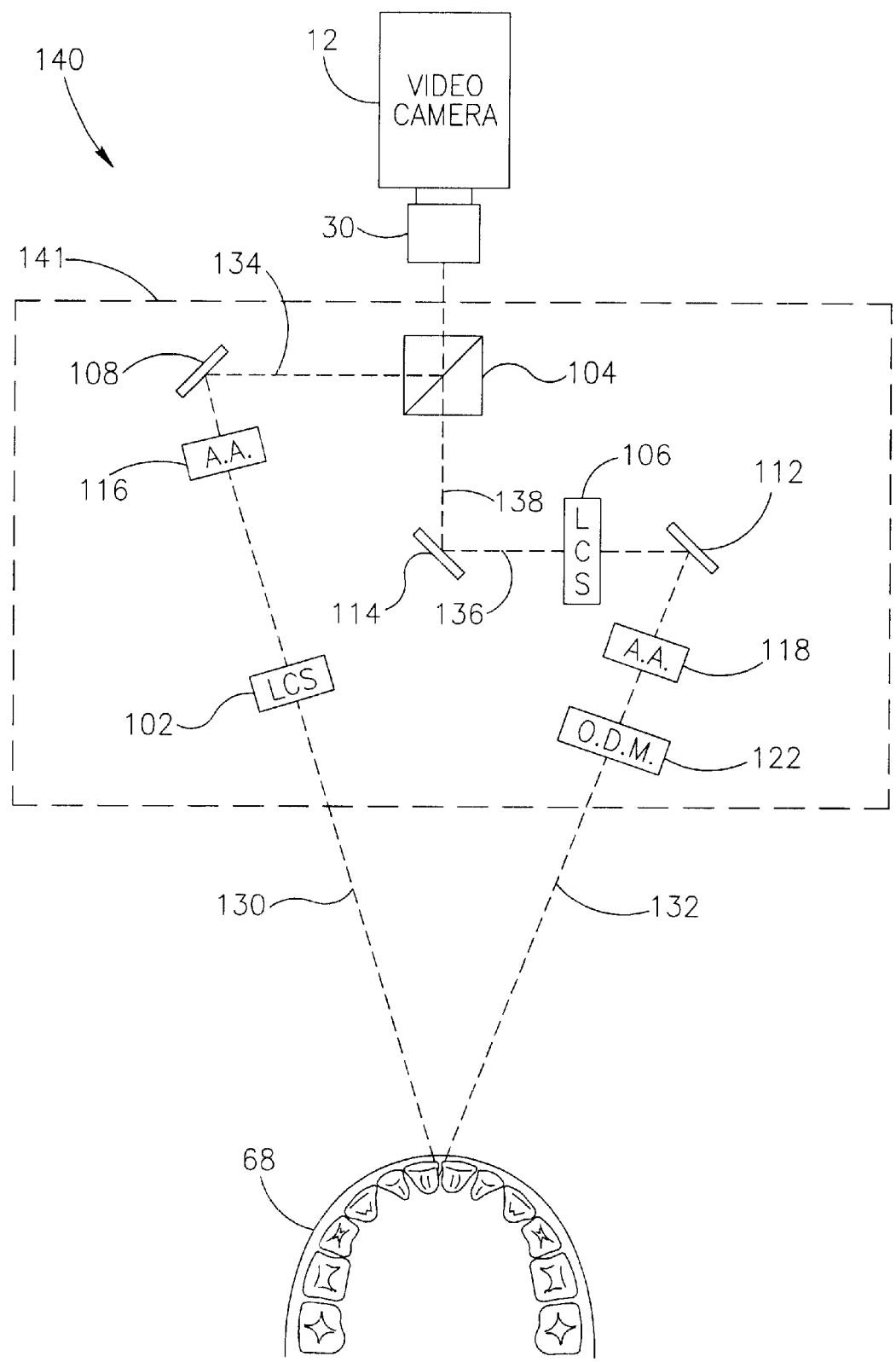

Reference is now made to FIGS. 8–10 which are schematic block diagrams illustrating three different configurations of imaging units which are parts of a stereoscopic 3D video system constructed and operative to enable 3D stereoscopic viewing of the oral cavity of patients in accordance with additional preferred embodiments of the present invention.

FIG. 8 illustrates a schematic top view of an imaging unit 110. The imaging unit 110 includes the video camera 12 and an optical assembly 111. The video camera 12 is attached to the lens assembly 30. The optical assembly 111 includes a BS 104 and an LCS 106 which are aligned along the optical axis 138 of the lens assembly 30. The optical assembly 111 also includes three folding mirrors 108, 112 and 114 which are arranged to provide two different optical axes 130 and 132. The video camera 12 can thus acquire an image of the oral cavity 68 along the optical axes 130 or 132 as disclosed in detail hereinbelow. The optical assembly 111 further includes an LCS 102 positioned between the BS 104 and the folding mirror 108 along the optical axis 134. The optical assembly 111 also includes an AA 116 positioned in front of the folding mirror 108 along the optical axis 130. The optical assembly 111 additionally includes an AA 118 and an ODM 122 positioned in front of the folding mirror 112 along the optical axis 132.

FIGS. 9 and 10 illustrate two imaging units 120 and 140, respectively. The optical assemblies 121 and 141 of imaging units 120 and 140, respectively, include the same parts as the optical assembly 111 of the imaging unit 110 of FIG. 8. The difference between imaging units 111, 121 and 141 is in the arrangement of the different parts along the optical axes 130, 132, 134, 136 and 138.

The imaging units 110, 120 and 140 operate by alternately switching the LCS units 102 and 106 between the first and second states in such a way that whenever the LCS unit 102 is in the first state, the LCS unit 106 is in the second state, mutatis mutandis. The switching is performed by the synchronizing unit 19 (not shown). When the LCS unit 102 is in the first state the light reflected from parts within the oral cavity 68 along the optical axis 130 is allowed to pass through the LCS unit 102 and reach the video camera 12, while the light reflected from the same parts within the oral cavity 68 along the optical axis 132 is prevented from reaching the video camera 12 by the LCS unit 106 which is in the second state.

When the LCS unit 102 is switched to the second state by the synchronizing unit 19, the light reflected from parts within the oral cavity 68 along the optical axis 130 is blocked from passing through the LCS unit 102 and does not reach the video camera 12, while the light reflected from the same parts within the oral cavity 68 along the optical axis 132 reaches the video camera 12 by passing through the LCS unit 106 which is in the first state.

The imaging units 110, 120 and 140 alternatively send to the video display 8 images of the parts of the oral cavity acquired from two different viewing angles which coincide with the optical axes 130 and 132. The synchronizing unit 19 adjusts the switching of the LCS spectacles 16 which are worn by the dentist 2 in such a way that the LCS 26 is switched to the first state and the LCS 28 is switched to the second state when the video display 8 displays the image acquired through the optical axis 132. The LCS 26 is switched to the second state and the LCS 28 is switched to the first state when the video display 8 displays the image acquired through the optical axis 130.

Thus, the operation of the imaging unit 110 or 120 or 140 in synchrony with the LCS spectacles 16 enables the 3D stereoscopic viewing of the oral cavity 68 by the dentist 2.

It will be appreciated by persons skilled in the art that various different arrangements of the components of the optical assemblies 22, 111, 121 and 141 disclosed hereinabove are possible by rearrangement of the positions of certain components, for example the positions of the AA 118 and the ODM 122 of FIG. 8 can be interchanged along the optical axis 132.

It is noted that in the imaging units 110, 120 and 140 are designed for stereoscopic 3D viewing and cannot operate in the photogrammetric mode of the imaging unit 15 of FIG. 1.

Figure 11:
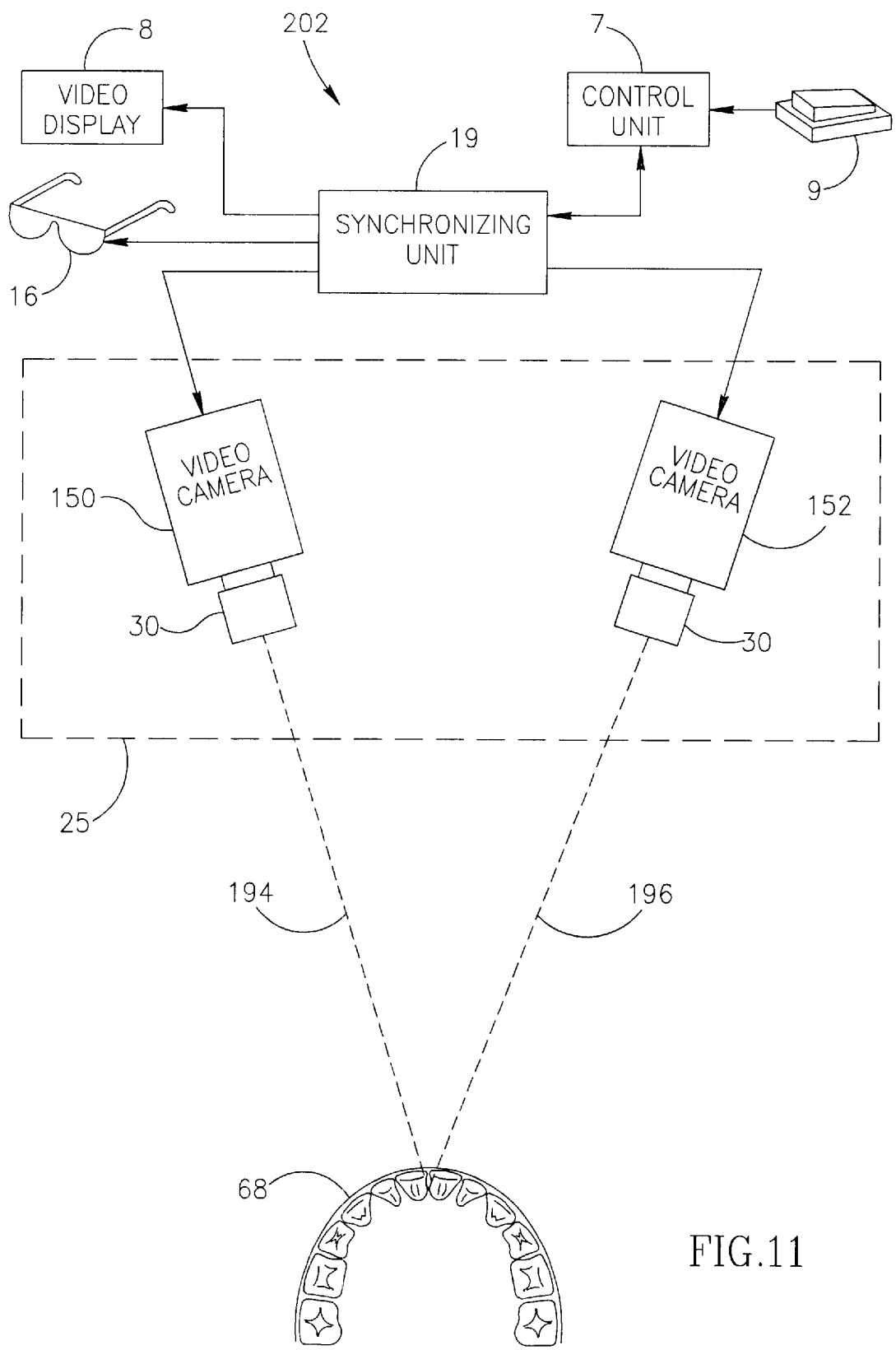
FIG. 11 is a schematic block diagram illustrating a 3D stereoscopic video system having two video cameras in accordance with yet another preferred embodiment of the present invention.

Reference is now made to FIG. 11 which is a schematic block diagram illustrating a 3D stereoscopic video system 202 having an imaging unit 25 including two video cameras in accordance with yet another preferred embodiment of the present invention.

Video system 202 includes a synchronizing unit 19, a video display 8, LCS spectacles 16, a control unit 7 and a foot pedal 9. Video system 202 also includes a head set (not shown) similar to the head set 10 of FIG. 1, except that two video cameras 150 and 152 of the imaging unit 25 are suitably attached to the head set. An additional difference between the video system 202 and the video system 5 of FIG. 1 is that video system 202 does not include the optical assembly 22 of FIG. 1.

Figure 12:
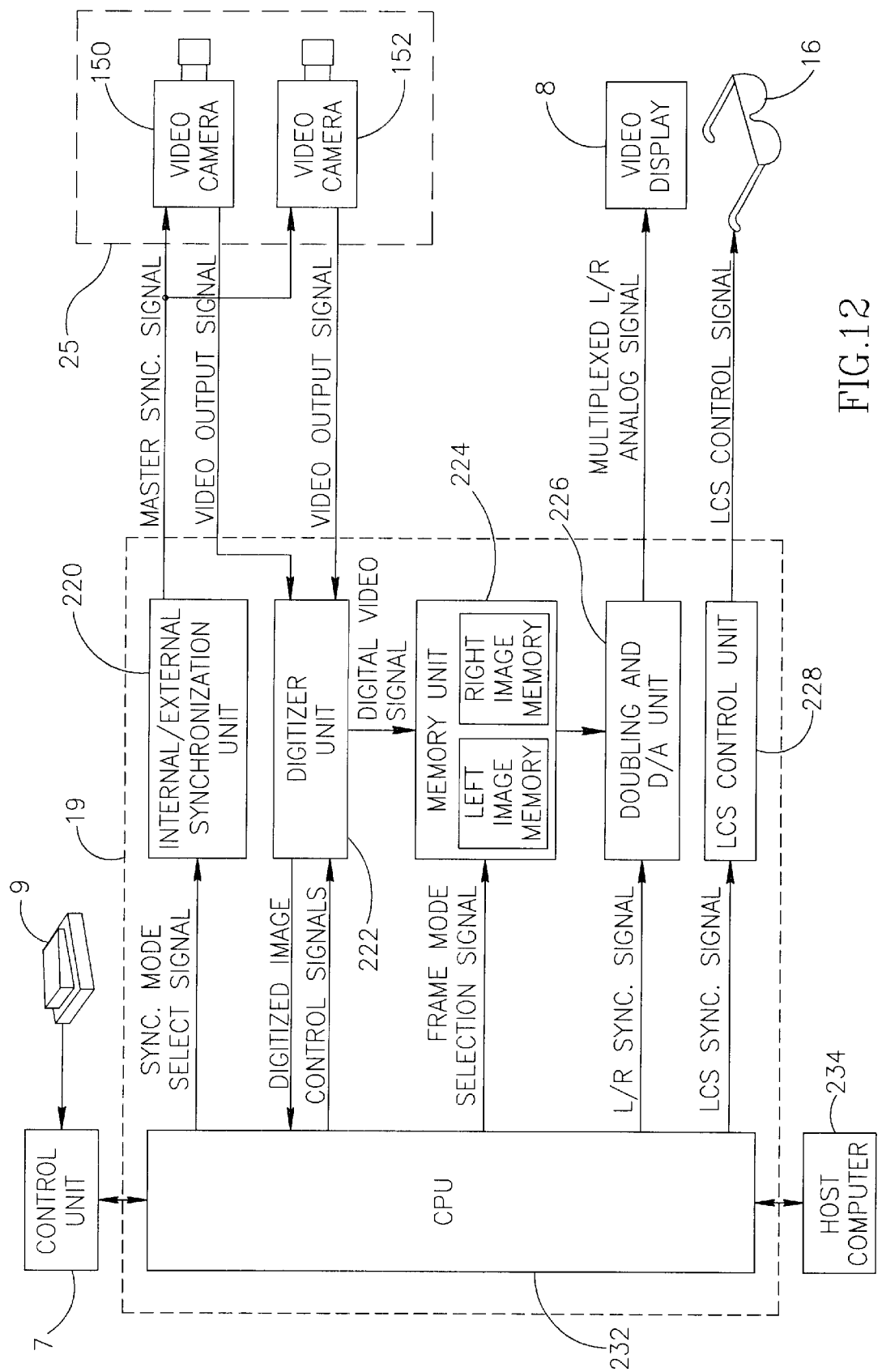
FIG. 12 is a schematic block diagram illustrating in detail the connections of the various components of the 3D video system of FIG. 11 in accordance with another preferred embodiment of the present invention.

Reference is now made to FIG. 12 which is a schematic block diagram illustrating in detail the connections of the various components of the 3D video system 202 of FIG. 11 and their mode of operation, in accordance with another preferred embodiment of the present invention.

The synchronizing unit 19 of FIG. 12, which is similar to that of FIG. 2, is connected to two video cameras 150 and 152. As best seen in FIG. 11 video camera 150 views the oral cavity 68 from the right along the optical path 194 and video camera 152 views the oral cavity 68 from the left along the optical path 196. However, the two video cameras can be interchanged.

When the synchronizing unit 19 is connected to two video cameras it operates differently than when it is connected to the single video camera 12 and the optical assembly 22 as disclosed hereinabove (FIG. 2). In the single camera operational mode disclosed for FIG. 2, the internal/external synchronization unit 220 synchronizes itself to the field rate of the video camera 12. In contrast, in the two cameras operational mode of FIG. 12 the internal/external synchronization unit 220 sends a master synchronization signal to video cameras 150 and 152 for synchronizing both of them to the synchronization unit 19. The digitizer unit 222 can digitize fields or frames from video cameras 152 and 150 and store the resulting digitized video images in the left and right image memory of the memory unit 224, respectively. The doubling and D/A unit 226, LCS control unit 228 and LCS spectacles 16 operate for generating a 3D stereoscopic image of the oral cavity 68 as disclosed in detail hereinabove.

It is noted that the system disclosed in FIGS. 11 and 12 cannot operate in the photogrammetric mode.

Figure 13:
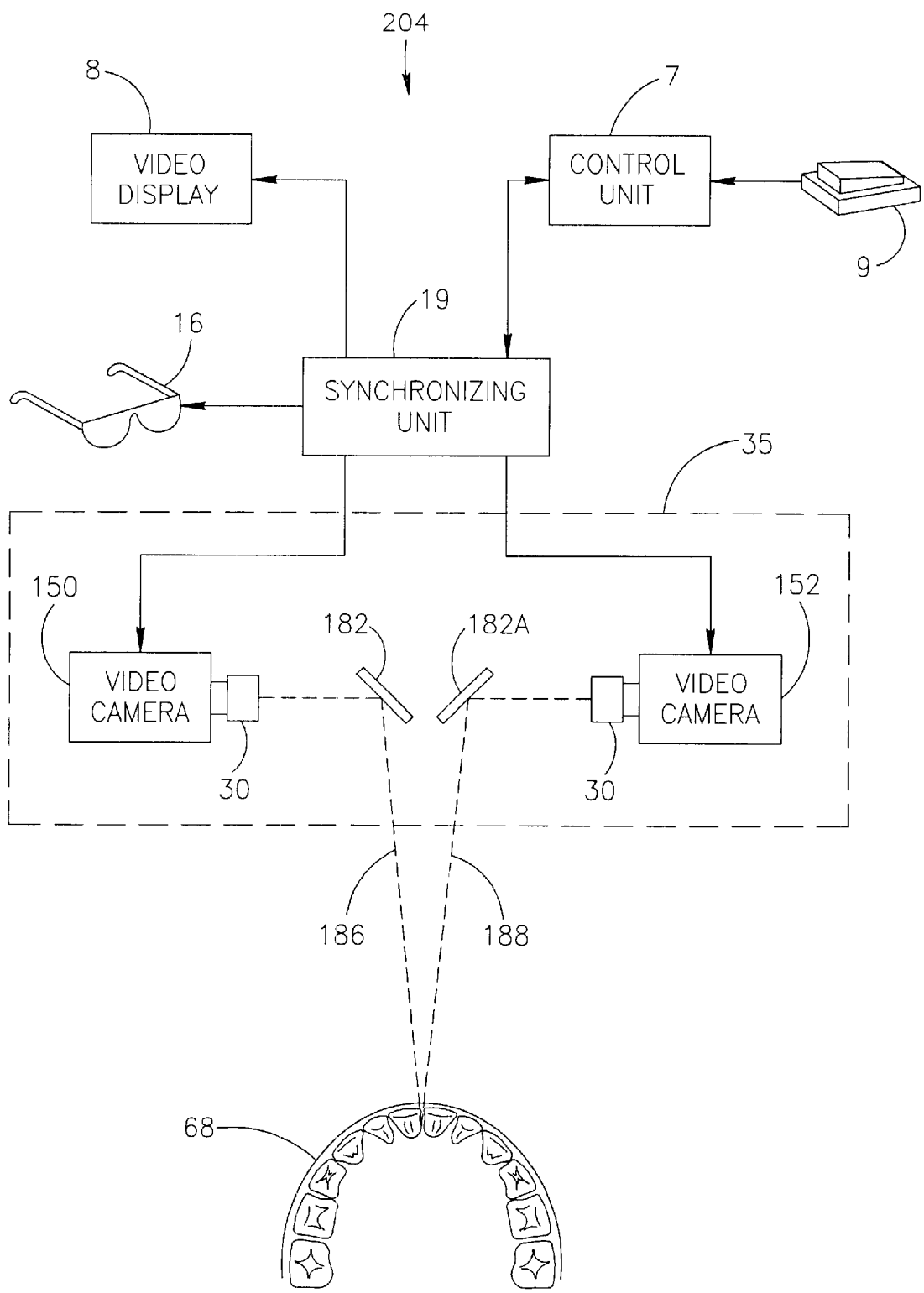
FIG. 13 is a schematic block diagram illustrating a 3D stereoscopic video system in accordance with another preferred embodiment of the present invention.

Reference is now made to FIG. 13 which is a schematic block diagram illustrating a video system 204 for stereoscopic 3D viewing in accordance with another preferred embodiment of the present invention. The imaging system 204 includes an imaging unit 35 which includes two video cameras 150 and 152 suitably positioned on the left and right sides of the patient. The imaging system unit 35 further includes two folding mirrors 182 and 182A. Each of video cameras 150 and 152 includes a lens assembly 30 and can acquire an image of the oral cavity from a different effective angle of view 186 or 188. The video system 204 also includes a control unit 7, a video display 8, LCS spectacles 16, a control unit 7 and a foot pedal 9 suitably connected to a synchronizing unit 19. The video system 204 operates similarly to the video system 202 as disclosed in detail hereinabove (FIG. 11).

Figure 14:
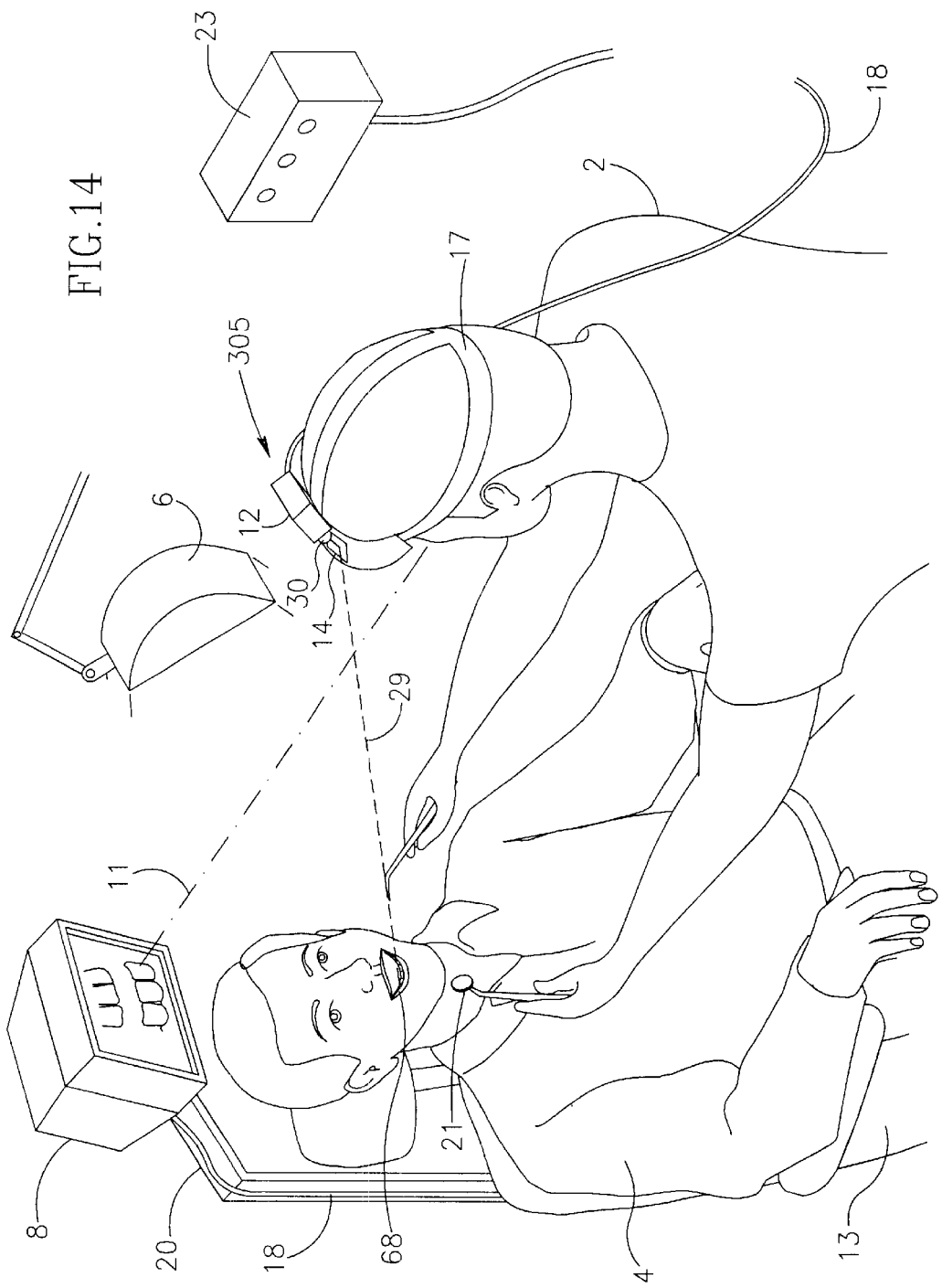
FIG. 14 is a schematic isometric view of a video system for two dimensional (2D) video imaging of the oral cavity of a patient in accordance with a preferred embodiment of the present invention.

Reference is now made to FIG. 14 which is a schematic isometric view of a video system 300 for two dimensional (2D) video imaging of the oral cavity of a patient in accordance with another preferred embodiment of the present invention. The video system 300 includes the light source 6, the video display 8, the chair 13 and the display stand 20 of FIG. 1. The video system 300 also includes a head set 305 and a control unit 23. The head set 305 includes the harness 17 of FIG. 1 and a video camera 12 attached to the harness 17. The head set 305 also includes a folding mirror 14 which is attached to the harness 17. The folding mirror 14 is positioned in such a way that the camera 12 can image the area including the oral cavity 68 along the line 29 when the dentist 2 looks at the video display 8 along the line of sight 11. Thus, the video system 300 provides the dentist 2 with a two dimensional image of the oral cavity 68 which is displayed on the video display 8. The two dimensional image can be suitably enlarged by using a zooming lens assembly 30 attached to the video camera 12 and controlled by the control unit 23.

Figure 15:
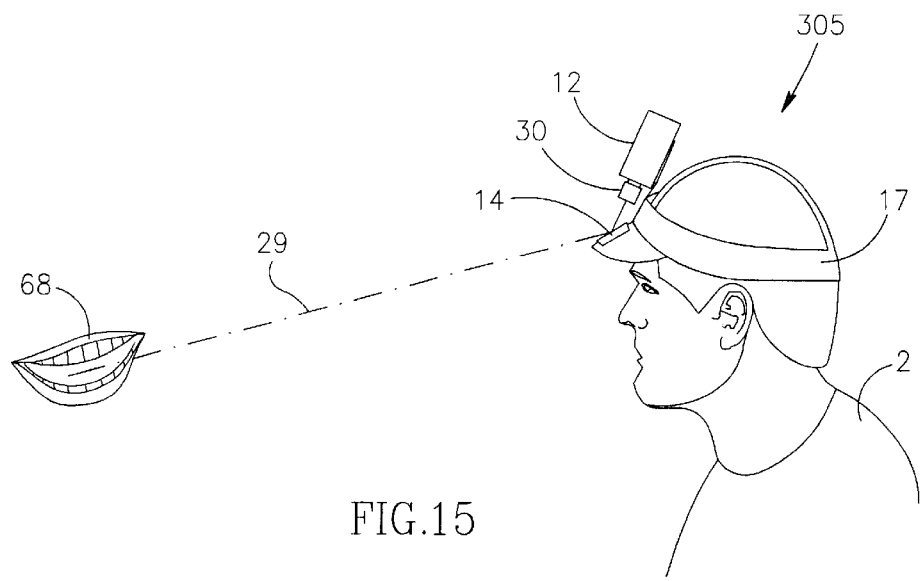
FIG. 15 is a schematic side view illustrating the head set of the video system of FIG. 14.

Reference is now made to FIG. 15 which is a schematic side view illustrating the head set 305 of FIG. 14. FIG. 15 illustrates the folding of light arriving from parts of the oral cavity 68 along the line 29 by the folding mirror 14 which reflects the light towards the lens assembly 30 of the video camera 12.

Going back to FIG. 14, it is noted that the system enables the dentist 2 to observe a magnified two dimensional image of the oral cavity 68 of the patient 4 on video display 8, while having both hands free to perform various operations within the oral cavity 68. The video system 300 additionally includes a control unit 23 for controlling the degree of magnification of the video image by the lens assembly 30 and the intensity of the image displayed by video display 8. The video system 300 also includes a foot pedal (not shown) for controlling the focal length of the zooming lens assembly 30 and various cables (not shown) necessary for connecting the video camera with the control unit 23, the video display 8 and the foot pedal.

Figure 16:
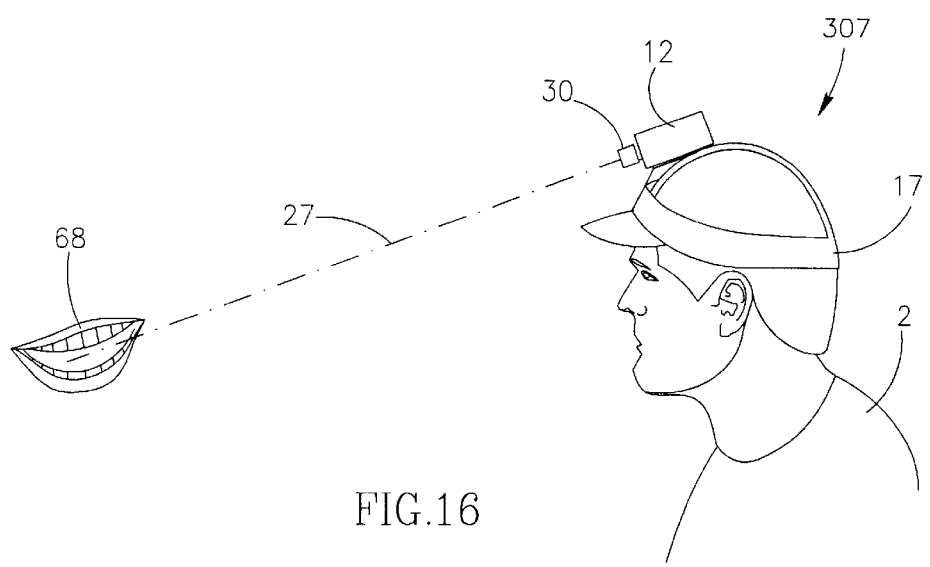
FIG. 16 is a schematic side view illustrating a different configuration of a head set that can be used in the video system of FIGS. 14 and 15 in accordance with yet another preferred embodiment of the present invention.

Reference is now made to FIG. 16 illustrating in detail a different configuration of a head set 307 that can be used in the video system 300 instead of head set 305 of FIGS. 14 and 15. The head set 307 includes the harness 17 and the video camera 12 which is attached thereto. The video camera is attached to the harness 17 in a way which allows for adjustment of the line of sight 27 of the video camera 12 by the dentist 2. This configuration obviates the need for the folding mirror 14 of FIG. 15.

It is noted that in all the preferred embodiments disclosed hereinabove and illustrated in the various figures the lens assembly 30 can be any suitable lens such as a lens with a fixed focal length, a lens with multiple focal length settings or a continuously variable zoom lens.

It is also noted that although the 3D video viewing system disclosed hereinbelow in accordance with the preferred embodiments of the present invention is adapted for use by dentists, certain aspects of the invention are equally applicable to other types of use. The system can also be generally adapted for use in any application where a system is needed to enable a person to view objects two-dimensionally or three-dimensionally on a video display, with or without zooming capability, while having both hands free to manipulate the objects and while retaining the possibility of direct visual contact with the viewed objects. For example the system can be used for inspection and repair of electronic circuit boards, for assembling or taking apart of multi-component mechanical devices such as watches or any other mechanical devices or for surgery.

It will be appreciated by persons skilled in the art that the present invention is not limited to what has been particularly shown and described hereinabove. Rather the scope of the present invention is defined only by the claims which follow:

What is claimed is:

1. A video system for providing an operator with a three dimensional stereoscopic image of the oral cavity of a patient, the system comprising:

an imaging unit for providing at least two stereoscopic images of said oral cavity;

a pair of switchable shutters for alternatingly blocking the view of the left eye and the right eye of said operator;

a synchronizing unit for synchronizing the switching of said pair of switchable shutters with the rate of generation of said at least two stereoscopic video images by said imaging unit; and a video display for displaying said at least two stereoscopic images.

2. A video system according to claim 1 wherein said imaging unit comprises:

a video camera; and an optical assembly disposed between said video camera and said oral cavity for alternatingly providing said video camera with at least two different stereoscopic images of said oral cavity in synchrony with the field rate of said video camera.

3. A video system according to claim 2 wherein said optical assembly is also operative to simultaneously provide a first image of said oral cavity along a first optical axis of said optical assembly, and a pair of second and third stereoscopic images of said oral cavity along a second and third optical axes of said optical assembly, respectively, wherein said second and said third optical axes are inclined at an angle to said first optical axis, and wherein said three different images are superimposed upon the imager of said video camera to provide a composite video image.

4. A video system according to claim 3 wherein said synchronizing unit also digitizes said composite video image and provides a host computer with a digitized composite video image for performing photogrammetric measurements thereon.

5. A video system according to claim 1 wherein said imaging unit comprises two video cameras providing a pair of stereoscopic images of said oral cavity, and wherein said synchronizing unit synchronizes said two video cameras with the switching rate of said switchable shutters.

6. A video system according to claim 1 wherein said imaging unit is attached to a harness worn on the head of said operator.

7. A video system according to claim 1 wherein said video system also comprises a folding mirror for folding the light reflected from said oral cavity towards said imaging unit.

8. A video system according to claim 5 wherein said imaging unit also comprises two folding mirrors for folding the light reflected from said oral cavity towards said two video cameras.

9. A video system according to claim 2 wherein said synchronizing unit provides multiplexed left and right video image signals to said video display at a rate which is double the field rate of said video camera for providing said operator with a flicker-free image of said oral cavity on said video display.

10. A video system according to claim 1 wherein said switchable shutters are liquid-crystal shutters.

11. A video system according to claim 2 wherein said video camera further comprises a zoom lens controllable by said operator for providing said three dimensional stereoscopic images at a selectable magnification.

12. A video system according to claim 2 wherein said video camera further comprises a zoom lens controllable by said operator for providing said composite video image at a selectable magnification.

* * * * *